United States Patent [19]
Wildman

[11] Patent Number: 5,154,606
[45] Date of Patent: Oct. 13, 1992

[54] LAMINATED ORTHODONTIC BRACKETS

[76] Inventor: Alexander J. Wildman, 2662 Donner Pl., Eugene, Oreg. 97401

[21] Appl. No.: 632,067

[22] Filed: Dec. 21, 1990

Related U.S. Application Data

[62] Division of Ser. No. 247,178, Sep. 21, 1988, Pat. No. 5,018,259.

[51] Int. Cl.⁵ ............................................. A61C 3/00
[52] U.S. Cl. ......................................................... 433/8
[58] Field of Search ..................... 433/8, 9, 10, 11, 12, 433/13, 14, 15, 16, 17

[56] References Cited

U.S. PATENT DOCUMENTS

| | | | |
|---|---|---|---|
| 3,128,552 | 4/1964 | Broussard | 433/13 |
| 3,307,261 | 3/1967 | Steiner | 433/15 |
| 4,256,455 | 3/1981 | Förster | 433/8 |
| 4,889,485 | 12/1989 | Iida | 433/9 |

*Primary Examiner*—John J. Wilson
*Attorney, Agent, or Firm*—Marger, Johnson, McCollom & Stolowitz

[57] ABSTRACT

A design and manufacturing process uses flat sheets with outline shapes cut into the metal to manufacture orthodontic parts in laminate form. These sheets are aligned and stacked together, tack welded and brazed together in a flat form or may be bent together and then brazed. The process may be used to produce either commonly used conventional orthodontic brackets or very complicated shapes required for difficult applications.

11 Claims, 7 Drawing Sheets

LAMINATED ORTHODONTIC BRACKETS

RELATED APPLICATION DATA

This application is a divisional of U.S. application Ser. No. 07/247,178, filed Sept. 21, 1988, now U.S. Pat. No. 5,018,259 issued May, 21, 1991.

BACKGROUND OF THE INVENTION

This invention relates to the fabrication of detailed dental appliances and more particularly to a method of designing and making orthodontic brackets and the like.

Heretofore, orthodontic brackets have customarily been made by die stamping, machining or casting. As the orthodontic art has progressed, the desire to make more intricate and smaller parts has been limited by the available materials and methods of fabrication.

In the past, gold was the material of choice for orthodontic brackets, but now stainless steel is usually used. The 300 series stainless steels are the most common materials selected for orthodontic attachments. Sometimes 17/7 and 17/4 stainless steels are used because these steels can be heat treated.

The tooling for stamped parts is expensive, but once it is built, the parts can be made relatively accurately and inexpensively. Stamping and forming requires the use of softer metals but this limitation can be overcome by using heat treatable metal such as 17/7 stainless steel in the annealed state. The part is then heat treated. Holes in stamped parts must be no smaller than the material thickness. In general, the more complex the parts, the more impractical die stamping and forming becomes.

Job shops that can make shapes in flat stock are readily available, but the stamping and metal folding needed to make complicated orthodontic attachments requires special manufacturing skills. At the present time, use of die stamping and forming is limited to flat parts such as lock pins and mesh foil bonding pads and to the manufacture of simple formed brackets for the Begg light wire technique and for some buccal tubes.

Metal machining is commonly used in the manufacture of orthodontic parts. Semi-soft, machineable grades of 300 series stainless are the preferred materials. Parts made from machineable grade stainless steel cannot be heat treated. Since these parts must remain semi-soft, strength becomes a problem in the manufacture of small cross sections.

Figure 1:
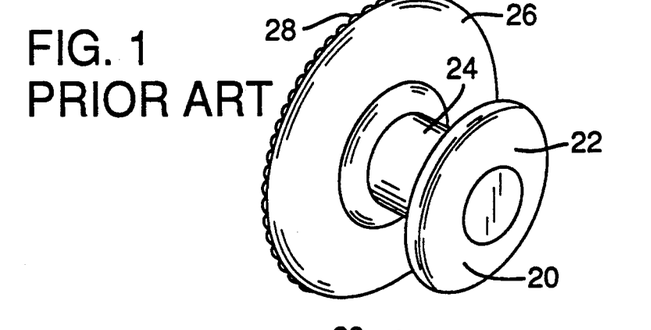
FIG. 1 is a perspective view of a prior art screw-machined orthodontic cleat.

Some orthodontic attachments such as a simple lingual button (FIG. 1) can be made on a screw machine. Screw machine job shops are readily available. Set up charges for a screw machine operation are inexpensive, but the cost per part is expensive. As the shapes of attachments become more innovative and complex and less available in the common job shop, the complicated tooling becomes very expensive.

The introduction of the lost wax investment casting process in the manufacture of orthodontic attachments has allowed parts to be designed that could not be made by die stamping and forming or by machining technologies. Wildman's Edgelok bracket (U.S. Pat. No. 3,780,437) is such an example. Orthodontic brackets made by the investment casting method begin as plastic patterns formed by injection molding. Very often this is high density polystyrene. The injection molds in which these patterns are formed are expensive to make but produce very accurate parts. Very intricate shapes can be produced. The investment process is time consuming and the cost per part is high. All parts are fully annealed as cast and are soft. If strength is needed, a heat treatable stainless such as 17/4 can be used. Investment casting to the tolerances required in the manufacture of orthodontic parts is very exacting and is not readily available from commercial job shops.

Sinter bonded powered metal is used in an injection mold and is a viable alternative to casting. A cost advantage in sinter bonding comes from the elimination of the investment step. Nonetheless, the molds must withstand the wear problem of molding the powered metal and are very expensive. Casting limits the design of brackets to shapes and cross sectional dimensions that can be reliably cast without voids and with sufficient strength for orthodontic applications.

Conventionally, bracket bodies are fabricated separately and then mounted as a discrete step on a mesh-foil bonding pad. This is typically done by spot-welding or by brazing with various solders, including 80-20 gold-copper and 82-18 gold-silver eutectics applied in wire or paste form.

The tendency in the art is to move toward automatic and releasable brackets and to applications, such as lingual orthodontics, that require a wider variety of part configurations. The increased complexity challenges the limits of casting techniques and materials. And, together with the need for many different parts, it makes the cost of manufacture prohibitive. It would be desirable for orthodontists to be able to have parts made on a custom or semi-custom basis. Clearly, however, the cost and complexity of making state-of-the-art orthodontic parts by current methods precludes having parts made locally.

Chemical etching, which is sometimes called chemical milling, is a metal forming technology that is known and used in other arts. Chemical milling is used extensively in the production of flat stainless steel parts and is readily available from commercial job shops. It is also used in the electronics industry for making printed circuit boards. In this process, a photographic tool or mask is made from a line drawing and an acid resistant layer is printed on a sheet of metal. When the sheet is dipped in an acid bath, the imprinted pattern is resolved in the acid, leaving untouched the metal that is protected by the resistant film. This process is relatively cheap. Very intricate complicated shapes can easily be produced. Hard materials can be shaped by chemical etching. By staggering the pattern of the printed resistant film, some areas can be etched on one side but not on the other. Chemical etching is limited to relatively thin flat stock.

In its conventional form, chemical etching is unsuited for making orthodontic attachments other than such things as lock pins made from flat stock. Accordingly, a need remains for a better process for making orthodontic brackets.

SUMMARY OF THE INVENTION

One object, therefore, is to improve and simplify the design and fabrication of orthodontic appliances.

A second object of the invention is to enable economical construction of complicated shapes of metal orthodontic brackets.

Another object is to reduce the tooling costs and per unit costs of fabricating new orthodontic bracket designs.

Yet another object is to enable reduction of feature dimensions (for example, cross-sectional dimensions and holes) and/or gross size of metal orthodontic brackets.

A further object is to avoid the dimensional and materials limitations of conventional methods of making orthodontic parts.

An additional object is to enhance the design options for orthodontic parts, particularly to make smaller, more versatile orthodontic brackets.

My invention is a design and manufacturing process for the production of metal orthodontic attachments and the like. This method includes defining a three dimensional shape of an orthodontic bracket having a base, a body and an attachment member formed in said body and segmenting the designed shape of the bracket along a plurality of spaced-apart surfaces to define at least two laminae. Each lamina has a thickness defining one dimension of the bracket body in accordance with the spacing of the surfaces and a peripheral edge face defining a second dimension of the bracket body. Two layers of metal, each having two opposite major surfaces and a thickness proportional to the spacing of a corresponding one of the laminae, are patterned with a boundary on each layer of metal corresponding to the peripheral edge face of the corresponding lamina in the design. Each of the layers of metal are sectioned along the patterned boundary to form layer components, preferably by chemical etching, so that each layer component has a thickness and a peripheral edge face matching the thickness and peripheral edge face of the corresponding lamina in the design. The layer components are assembled in accordance with the segmented shape of the bracket design. Their major surfaces are positioned in contacting relationship and their peripheral edge faces in the same relative alignment as the edge faces of the laminae in the segmented shape of the bracket design. Then the assembled layer components are fused together, and preferably simultaneously to the base or bonding pad, at interfaces of said major surfaces.

The fusing step preferably includes applying preferably by plating, a brazable metal layer, such as gold-copper eutectic, to major surfaces of the layer components prior to assembly and brazing the layers together after assembly.

Using chemical etching for the patterning and sectioning steps includes masking an area of at least one major surface of each layer of metal within said boundary and selectively chemical etching away metal from the layer in areas exposed around the masked areas. Either or both major surfaces of the layer can be masked within selected portions of a layer so that the metal within said portions remains unetched or one side can be left exposed to half-etch such portion.

The laminae formed by segmenting the shape of the bracket body and the layers of metal used in fabrication of the bracket can be flat throughout all steps or can be curved, by forming the metal layers during or following the sectioning step. Preferably, the layers of metal are patterned and sectioned in strips or sheets, each comprising a plurality of replicated layer components interconnected by runners. Indexing holes can be formed in the runners of successive layers and used for aligning the components for assembly by inserting an indexing pin through the indexing hole of each layer.

The foregoing method provides great freedom of design and inexpensive manufacture of orthodontic brackets without substantial tooling cost. An individual orthodontist, or a group of like-minded orthodontists such as a study club, could design and inexpensively manufacture virtually any desired attachment. The design and manufacturing process requires no equipment or process that is not readily commercially available. Commercial job shops are available in most larger cities to perform chemical etching, plating, tooling of an assembly welding fixtures and vacuum brazing. The price of creating a part with this process would be within the resources of an orthodontist or at least a small group of orthodontists.

The foregoing and additional objects features and advantages of the invention will become more readily apparent from the following detailed description which proceeds with reference to the accompanying drawings.

DETAILED DESCRIPTION

General Description of Method

In this process, the shape of the attachment is designed so that two or more stacked layers determine the shape of the part. The sum of the thickness of the layers determines a dimension of the part perpendicular to the layers. The other two dimensions of the part are determined by the outline shape of each individual layer which are formed independently. The layers are aligned, one layer to another, and positioned precisely in a welding assembly fixture, and tack welded and then brazed in a vacuum or hydrogen atmosphere. The brazed layers become one laminated part. In the simplest form of the method, the layers are allowed to remain flat. In more advanced applications, the layers can be bent or formed before brazing to produce a greater variety of shapes.

Die stamping and photochemical etching are suitable ways to form outline shapes in flat stock. In high volume, parts are made cheaply using stamping, but die stamp tooling is relatively expensive. Chemical etching is the preferred embodiment in many cases. Almost any shape that can be drafted on paper can be reproduced as a finished metal layer. The tooling is very inexpensive. Additional architecture can be incorporated by etching one side only in selected regions, producing depressions that are half the thickness of the stock.

When a part is designed so the components of the part consist of flat layers, both the design and manufacture of orthodontic parts become very simple. As the designer outlines the part, he slices the elements of the part into flat or curved layers. The design proceeds to a drawing of each layer which is conveniently 20× actual size. Chemical milling job shops that will turn these drawings into flat metal parts are readily available. The cost of this operation is inexpensive. Preferably, for ease of later processing and economic production of many parts, each layer components of a single part is replicated many times in a sheet of flat stock. This is conveniently done by conventional photo-reproduction techniques.

The next step is to plate onto the formed flat layers first a very thin (e.g., on the order of a few microns) layer of copper and then a very thin layer of gold. The preferred ratio of the thickness of the layers is 20% copper to 80% gold by molecular weight. The metal forms an eutectic braze which is used at a later step in the process to fuse the layers together.

The next step is to assemble the layers in an assembly welding fixture. This fixture can be assembled by commercial tool makers. The electrodes of such fixture can be arranged to fit into a spot welder of the type that most orthodontists own.

Brazing is done preferably in a vacuum atmosphere without flux by a commercial vacuum brazer. After brazing, the assembled parts are separated from one another along their respective outlines. The parts can then be tumbled and would be ready to use.

In disclosing the details of this method, two examples are used. The first example is a lingual button. A screw-machined conventional lingual button (FIG. 1) is redesigned by my new method and will look like the drawing in FIG. 2 after manufacturing. The component parts of the lingual button 20 are the base 24 and the elastic retaining button 22. The screw-machined base and button are brazed to a mesh 28 foil pad 26. The detailed description shows how the base 24 and button 27 components are converted to layers.

Figure 7:
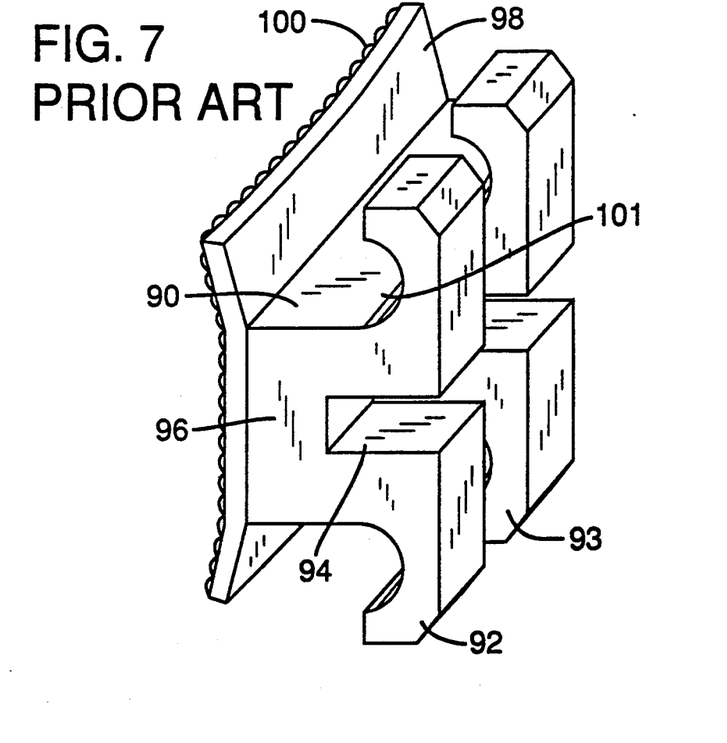
FIG. 7 is a perspective view of a prior art machined siamese edgewise orthodontic bracket.

The second example is a common machined twin wing edgewise bracket (FIG. 7) which is redesigned and manufactured by the new method. It will look like the drawing in FIG. 8. Example 2 shows how the layers are formed in the dimension of their thickness as well as peripherally, so that they will nest together before brazing. The method can thereby form a new version of the twin wing edgewise bracket. The new version 91 can be much stronger and smaller than the machined 90 form because it can be made of heat treated 17/7 stainless steel.

Example 1

Figure 2:
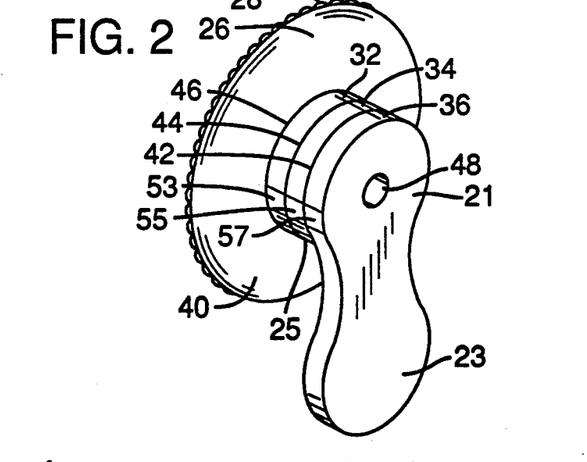
FIG. 2 is a perspective view of an orthodontic cleat designed and fabricated by the method of the present invention.

FIG. 2 shows a lingual cleat 21 designed and manufactured by the method of the invention. This lingual cleat 21 is analogous to the commonly used lingual button 20 made on a screw machine. The lingual cleat consists of a common orthodontic mesh 28 and foil 26 bonding pad and three layer components 32, 34, 36 designed so that when they are brazed together at interfaces 42, 44 and to the top surface 40 of pad 26 at interface 46, they form a complete part. The two layer components 32, 34 next to the pad become the base 25 of the lingual cleat 21 and are analogous to the base 24 of the lingual button 20. The third layer component 36 forms an elastic, oblong retaining member 23 which is more useful than circular button 22 of the common screw machine lingual button 20.

Figure 3:
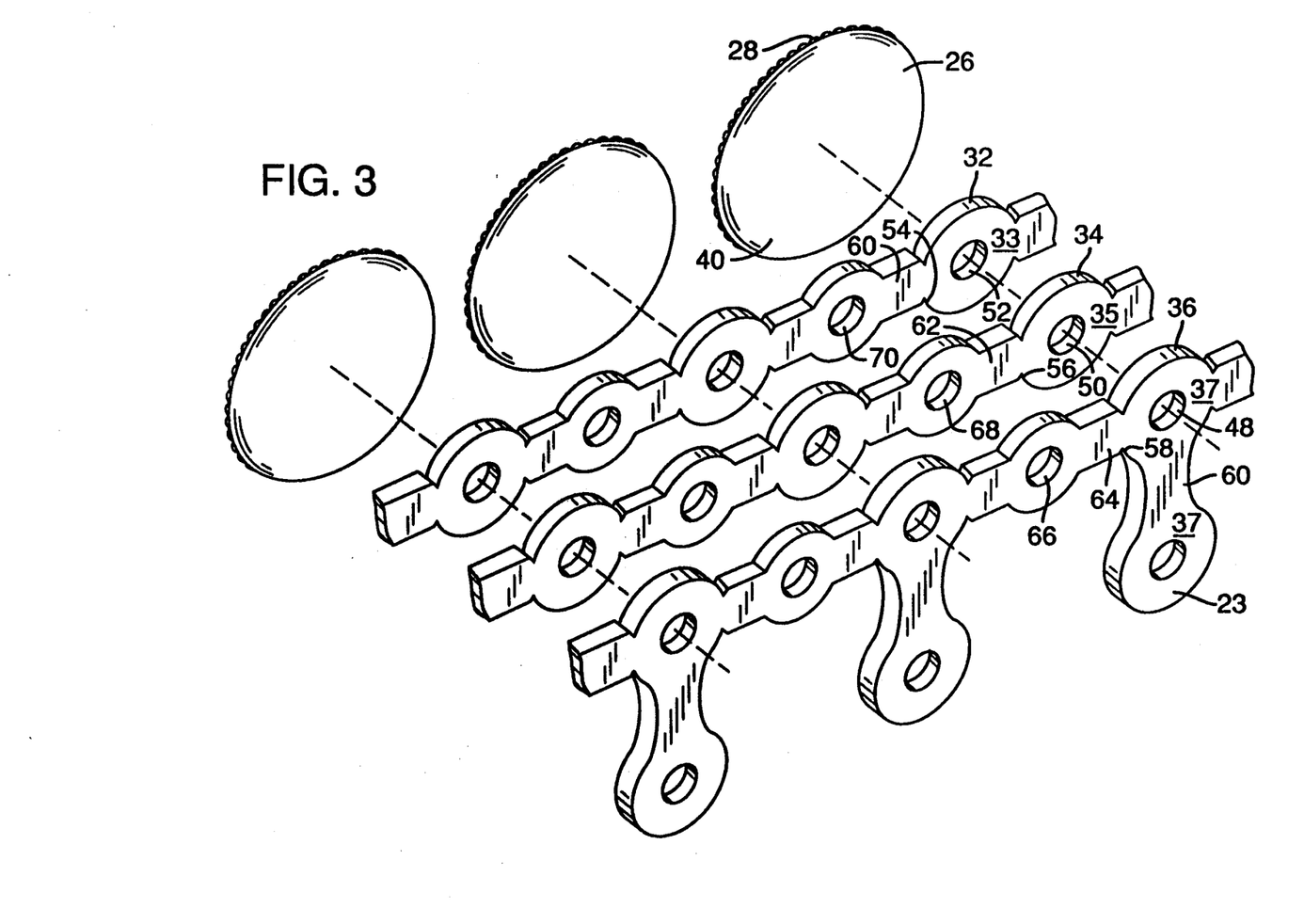
FIG. 3 is a perspective view of an intermediate step in the assembly process used to make a plurality of the cleats of FIG. 2.

FIG. 3 shows a projection view of the layer components as they would be oriented just prior to insertion in an assembly fixture. Each of the three layer components 32, 34, 36 are connected to like components with runners 60, 62, 64 so the parts can be processed in continuous strips, increasing manufacturing economy. The runners contain index holes 66, 68, 70 to receive index pins 72 of an assembly welding fixture, shown in FIG. 4 and FIG. 5. The runners of each layer are connected to the components 32, 34, 36 by a constricted notch 54, 56, 58 in the runner. These notches have the thinnest width in the runner strip and act as a breakoff point when the parts and the runners are separated. Regions 53, 55, 57 in FIG. 2 indicate the breakoff points in the finished part after detachment of the runners.

The layer components are ultimately fused by gold and copper eutectic braze plated on the strips, but first they must be assembled in proper orientation and tack welded together preparatory to brazing. The assembly welding tool (FIG. 4 and FIG. 5) is made from a block 74 of suitable plastic such as Delrin. A relative non-conductor of electricity must be used so that current can flow from the welder electrodes 78, 80 directly through the components to be welded. For the breakoff system to work well, the pads 26, 28 must be fixtured separately without runners so the pad foil 26 will braze to the body parts 32, 34, 36 and not to the runner system 60, 62, 64. Therefore, a pocket 76 is designed in the base 74 of the welding assembly fixture that is configured to receive the pads in a slightly convexo-concave condition and to hold the pad in proper orientation with the convex foil side 26 facing the three layers. The bottom of the pad pocket 77 contains a hole 79 slightly smaller than the size of the pad. This hole accepts one electrode 80 of an electric spot welder.

Figure 4:
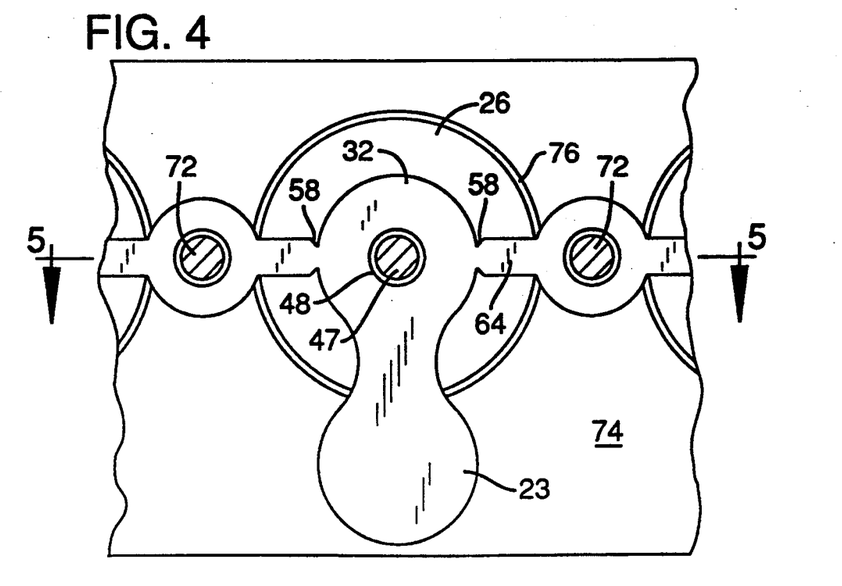
FIG. 4 is a plan view of a portion of the assembly of FIG. 3 positioned in a welding assembly fixture.
Figure 5:
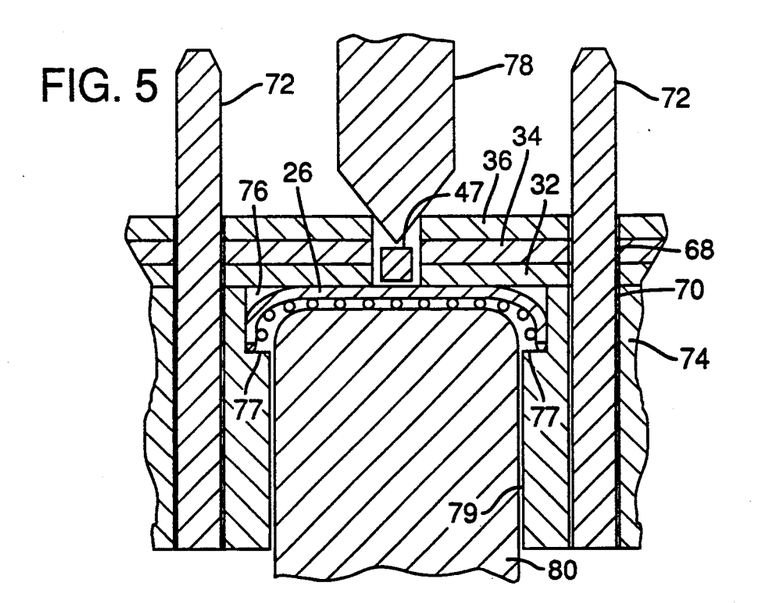
FIG. 5 is a cross-sectional view taken along lines 5—5 in FIG. 4 showing the electric spotwelding step of the assembly process.
Figure 6:
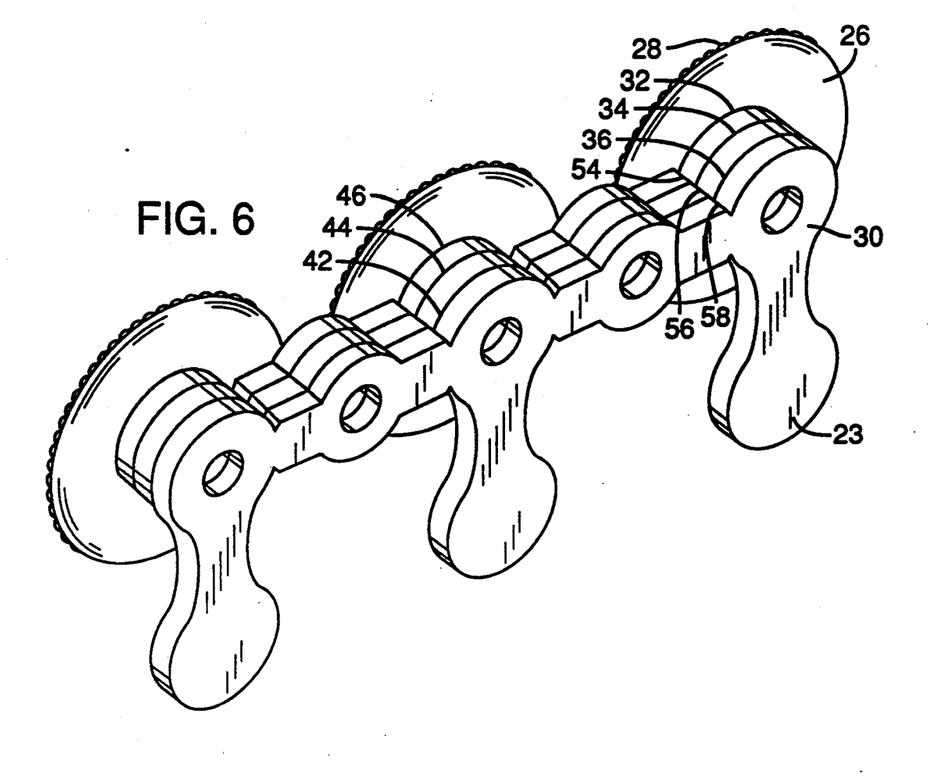
FIG. 6 is a perspective view of the assembled parts after the welding step of FIG. 5 and a subsequent vacuum-brazing step.

The block 74 of the welding assembly tool is fitted with indexing pins 72 to maintain orientation of the layers. The three layers 32, 34, 36 are then inserted into the fixture with the use of the index pins 72 which fit into the indexing holes 66, 68, 70 of the layers. The two body layers 34, 36, which are identical in this example, are inserted first and then the lingual cleat layer 32 is inserted into the fixture with the index pins inserted into the indexing holes. A small piece of braze or solder 47 is inserted into the hole formed by aligning the three holes 48, 50, 52 in the layer components of the part in each of the three layers.

An electric spot welding machine is used to join the fixed components. A base electrode 80 is then inserted into the base pad electrode hole 79. The opposing electrode 78 is inserted into the solder hole 48 of the elastic retaining cleat layer 36. The electrode 78 applies pressure, forcing the layers together, and is then activated to spot weld the layer components of the part into place. The welding electrode pressure and the welding current should be adjusted so that the gold braze 47 in the solder hole 48, 50, 52 is retained in the hole with the flash and metal distortion of the weld. An alternative method is to place the solder into the hole just before brazing. The weld should be strong enough to hold the pad and the three layers in proper orientation during brazing.

The brazing operation is done in a hydrogen atmosphere or preferably in a vacuum atmosphere. Job shops that provide this service are readily available.

To facilitate brazing the pad and the layers should be plated prior to assembly first with copper and then with gold. The proportionate thickness of the copper and gold plated layers should be 20% copper and 80% gold by molecular weight. Standard plating procedures as outlined in Table 1 are preferable.

TABLE 1

| | PLATING | |
|---|---|---|
| Process Step | Chemical | Concentration |
| 1. Solvent degrease | | |
| 2. Anodic electroclean (for 2-3 min.) | Oakite 90 | 8-12 oz/gal 40-60 lbs |
| 3. Rinse-clean (cold running water) | | |
| 4. Cathodic electro-activate 50% H.C.L. and 50% water for 30-60 sec. | Muriatic Acid | 50% 40 gal |
| 5. Rinse-clean (cold running water) | | |
| 6. Alkaline cyanide copper plate for 10-25 sec. at 5-15 amps per square foot to obtain .000004-.000010" thickness | Copper Cyanide | 3-4 oz/gal 30-40 lbs |
| | Sodium Cyanide | 3.5-4.25 oz/gal 35-50 lbs |
| | Roplex Cu | 2-4% by vol 3.2-6.4 gal |
| | Sodium Carbonate | 3.0-4.0 oz/gal 35-45 lbs |
| 7. Rinse-clean (cold running water) | | |
| 8. Acid gold plate 60-90 sec. at 5-10 amps per square foot to obtain .000012-.000016" thickness | Potassium Gold Cyanide | .44-.73 Toz/gal 6.5 Toz |
| | Potassium Citrate | 4.8-8.0 oz/gal 4.5 lbs |
| | Citric Acid | 2.8 lbs |
| | Ni Brightner | .8-.9 gm/liter 342 mls |
| | Mono K Phosphate | 10 oz/gal 5.6 lbs |
| 9. Rinse-clean (cold running water) | | |
| 10. Dry and pack | | |

The gold braze added to the solder hole 48, 50, 52 should also be 80% gold and 20% copper braze. Plating the layer components and pad for brazing assures that all contacting surfaces are wetted with braze. This can be enhanced by adding braze adjacent the interface of the layers and provides a reservoir of braze that is wicked into the interface areas.

The mesh 28 and foil 26 pads would preferably be die stamped to shape because chemically milling the mesh material is difficult and the shape of the pad is quite simple. The layer components 32, 34, 36 might be die stamped but would preferably be chemically milled because tooling costs would be much less expensive for these complex parts. Die stamping of simple shapes and chemical milling are both technologies readily available in job shops.

Example 2

Figure 8:
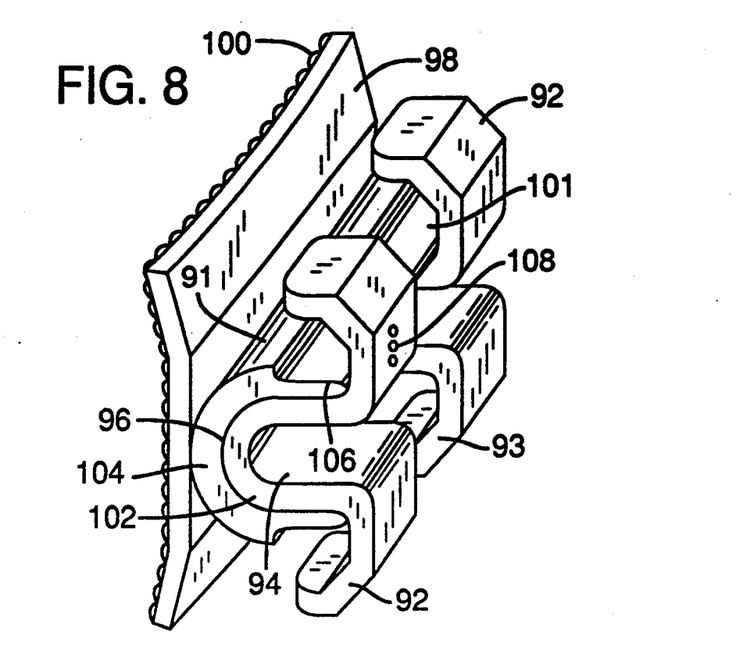
FIG. 8 is a perspective view of a siamese edgewise bracket designed and fabricated by the method of the present invention.

The design and manufacturing process may be used not only to make orthodontic attachments of simple shapes like the lingual cleat just described, but also more complicated shapes such as a twin winged bracket. FIG. 8 shows a conventional twin wing edgewise bracket 90 manufactured by machining.

A twin wing edgewise bracket contains two sets of tie wings 92 separated by a space 93. The tie wings provide a tie area 101. The tie wings are attached to the main body of the bracket 96 which contains an arch wire slot 94 which accepts an arch wire 95 (FIG. 9A, 9B, 9C).

Figure 9A:
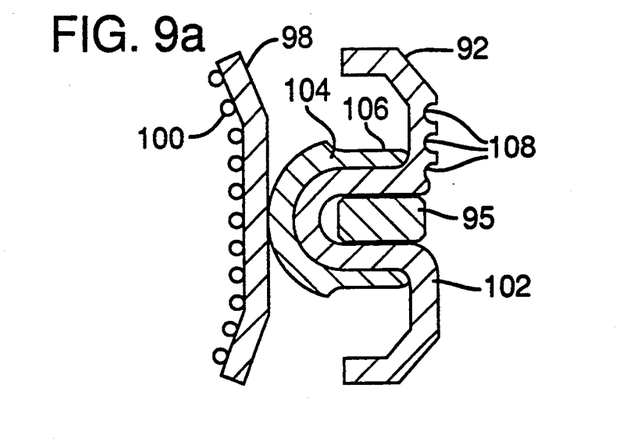
FIGS. 9A, 9B and 9C are side (mesial-distal), front (labial) and top (inciso-occlusal) views of the bracket of FIG. 8.
Figure 9B:
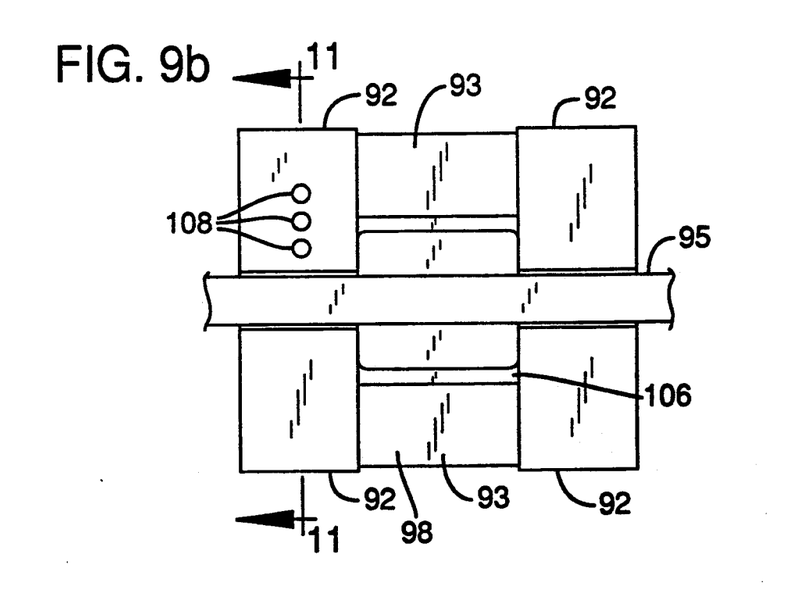
Figure 9C:
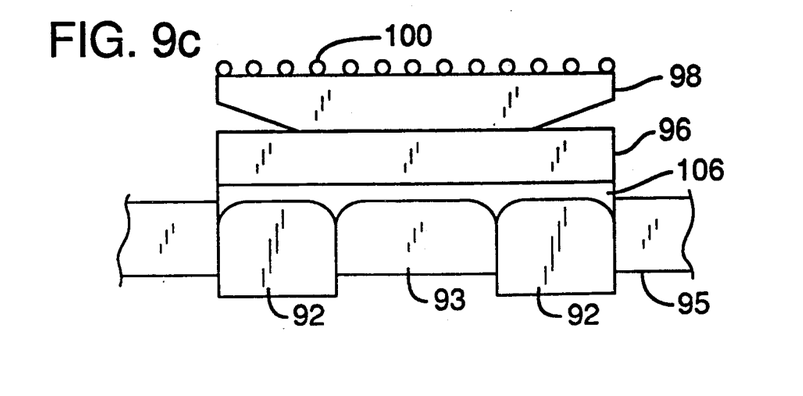

FIGS. 9A, 9B and 9C show a twin wing edgewise bracket 91 designed and manufactured by the new design and manufacturing method described here. Both the machined bracket and the new method bracket are gold brazed to a conventional bonding pad 98 which has mesh 100 that is diffusion bonded to the pad.

Figure 10A:
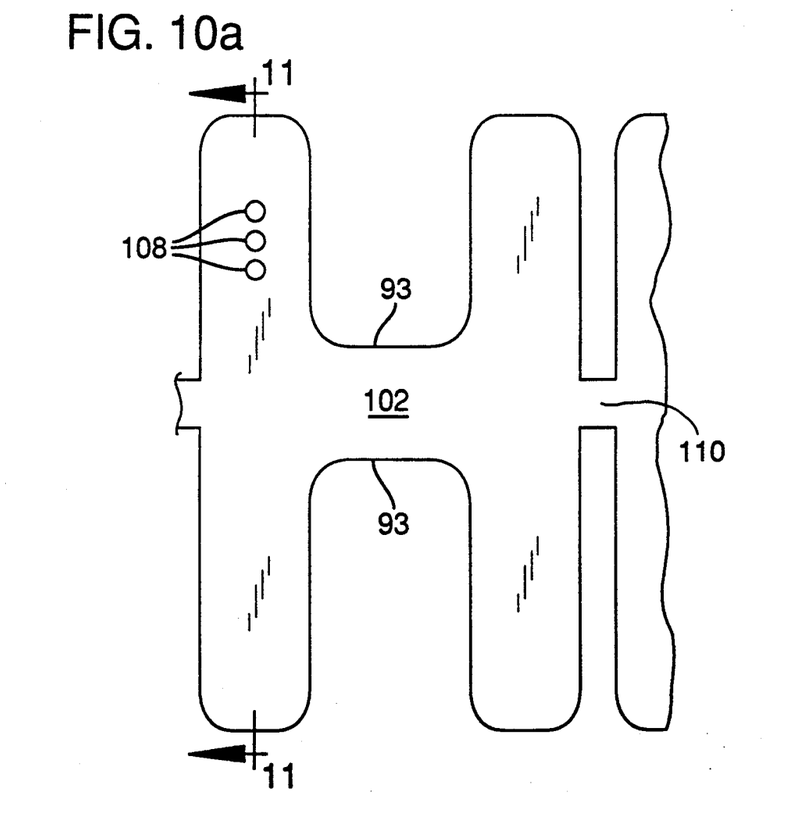
FIGS. 10A and 10B are plan views of the layer components of the bracket of FIG. 8 shown in a flat condition in an intermediate step of the assembly process.
Figure 10B:
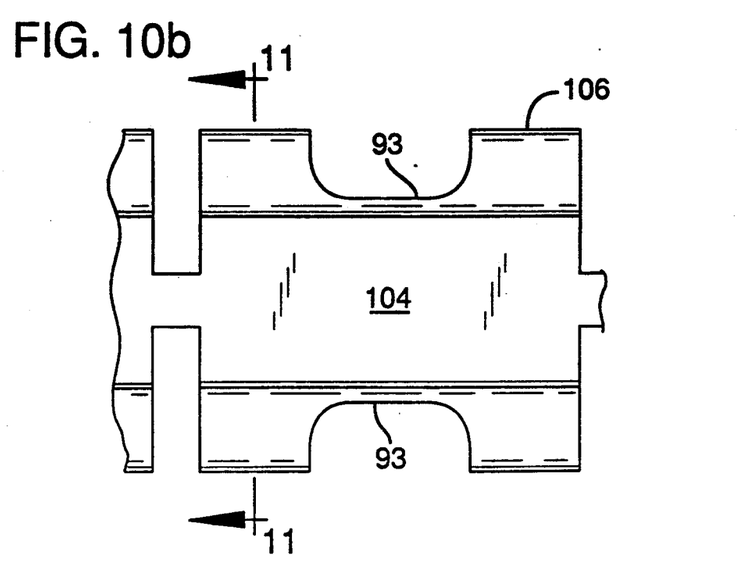

The design and manufacturing process for the twin winged bracket 91 is essentially the same as has been described for the fabrication of the lingual cleat 21 with two additional steps. The layer components are formed to define the arch-wire slot and wings and half etched to provide additional architecture. The flat layers are chemically milled to the designed shapes of layer components 102, 104 shown in FIG. 10A and FIG. 10B. Then the layer components are formed in the dimension of their thickness so that the inside layers 104 can nest in the outside layer 102 forming the archwire slot 94 and the body of the bracket 96 and the recurved wings 92. One or more layer components may be designed so that a portion of the metal is etched off of a given area to half the thickness of the layers in the chemical milling process. In making bracket 91, region 106 of layer 104 was half-etched to form the tie area in the wing 101 of the twin bracket 91. Half etching was also used to print identification marks 108 on the wing 92 of the bracket.

Figure 11:
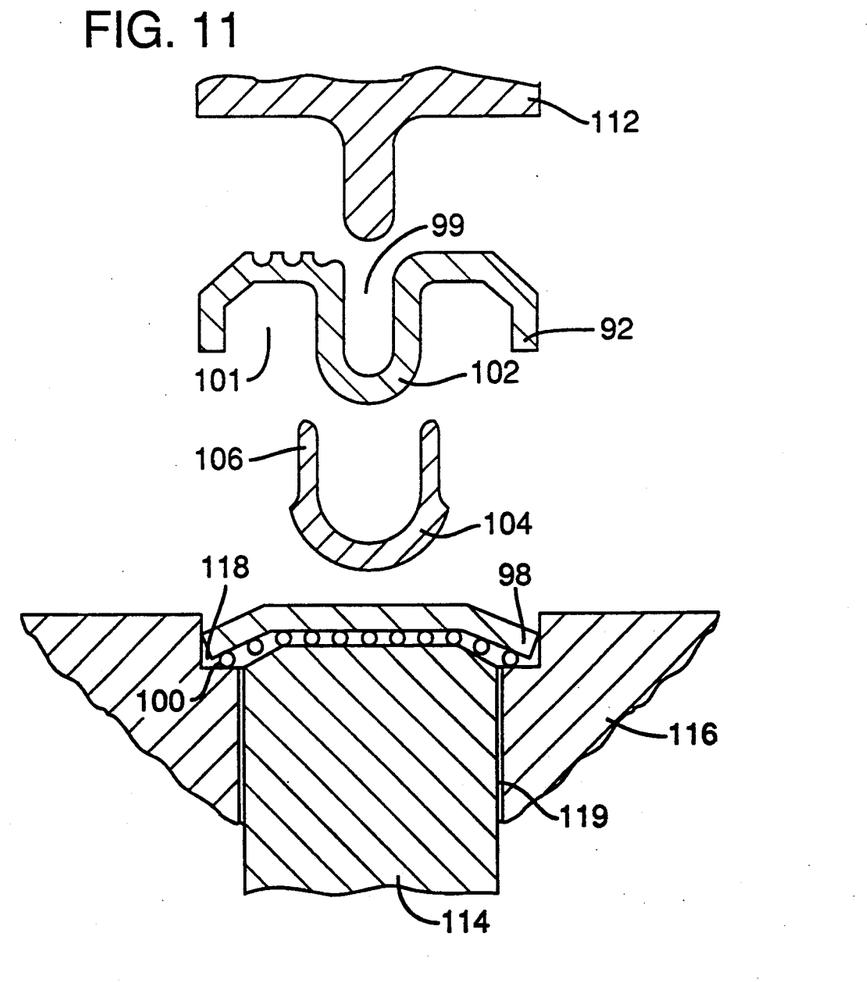
FIG. 11 is a cross sectional view taken along lines 11—11 in FIG. 9B, showing the bracket parts after forming the layer components, preparatory to spot-welding the parts to the pad.

The welding assembly fixture shown in FIG. 11 is similar to the fixture used in Example I. It consists of a plastic block 116 with a pad pocket 118 that receives the pad 98. The pad pocket has a receptacle 119 for an electrode 114 from a spot welder 114. The upper electrode 112 is configured to fit into the arch wire slot 94 of the formed part 102. The formed part then fits into the outside layer 104 and is held against the pad by the pressure of the electrodes as may be seen in FIG. 11. The same runner strip and indexing system could be used for this part as was used in Example 1.

After the parts are welded they are vacuum brazed in the same way as the parts in Example 1. The strength of the braze joint between layer component 104 and the foil layer 98 can be enhanced by wrapping a thin wire of the braze (8020 AuCu) around the interface of such layers before vacuum brazing.

By changing the angle of the electrodes, different slot angles in the base can be created.

Figure 12:
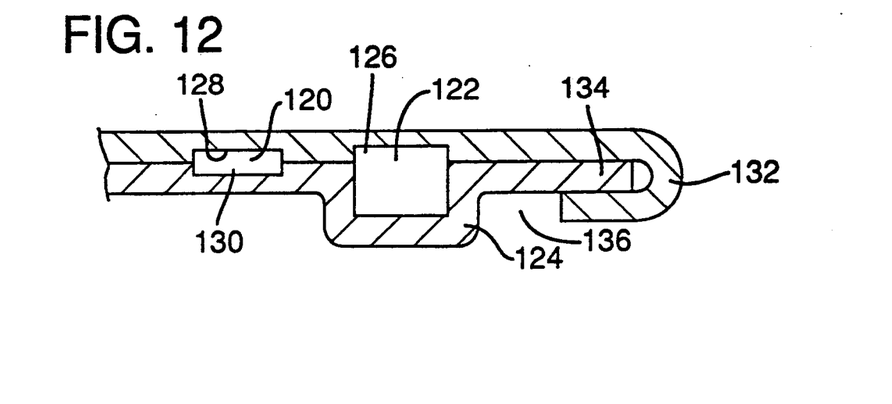
FIG. 12 is a third example showing additional orthodontic appliance structures that can be made by the invention.

Having illustrated and described the principles of my invention by way of two examples, it should be apparent that the invention may be modified in arrangement and detail and can be applied to a wide range of orthodontic appliances, without departing from such principles. FIG. 12 shows additional useful structures that can be formed in accordance with the invention. A rectangular hole 120 is formed by half-etching opposing faces of two layers to form opposed depressions or channels 128, 130. A larger hole 122 can be formed by combining half-etching a slot 126 in one layer and forming the other layer to create an opposing slot 124. A shoulder-type configuration can be made by folding a margin 132 of one layer around an edge 134 of the other layer. A slot 136 is formed between the edge of the wrapped margin 132 and the side of formed region 124.

I claim all embodiments and modifications falling within the scope and spirit of the following claims.

1. An orthodontic attachment construction comprising:
   a base for attaching the attachment to a surface of a tooth;
   a body mounted on the base and having a three-dimensional shape that defines an archwire slot and includes an attachment member for securing an archwire therein;
   the body being formed of at least two discrete layers of metal, each layer having two opposite spaced-apart major surfaces and a predetermined thickness defining a portion of at least one dimension of the body in accordance with the spacing of the surfaces and a peripheral edge face defining a second dimension of the body;
   means for fusing the layers together along said major surfaces; and
   the attachment member being integrally formed together with said body from at least one of the layers, the attachment member including a portion that protrudes in the second dimension outwardly from said body.

2. An orthodontic attachment construction as in claim 1 in which the periphery of one of the layers forming the body and the periphery of the layer forming the attachment member defines a discontinuity therebetween.

3. An orthodontic attachment construction as in claim 1 including a structural feature defined by a portion of one of the layers formed to approximately half of the predetermined thickness of the layer.

4. An orthodontic attachment construction as in claim 1 in which at least one of the layers comprises a curved layer.

5. An orthodontic attachment construction as in claim 1 in which the major surfaces of the metal layers include a brazable metal layer of a composition suited to orthodontics.

6. An orthodontic attachment construction as in claim 5 in which the metal layers are stainless steel layers and the brazable metal layer is a gold eutectic layer.

7. An orthodontic attachment construction as in claim 6 in which the brazable metal layer is a plated layer of 20% copper and 80% gold.

8. An orthodontic attachment construction as in claim 1 in which the base includes a mesh bonding pad.

9. An orthodontic attachment construction as in claim 1 in which the metal layers include alignment holes aligned along a common axis extending through the layers and the means for fusing includes a quantity of solder that substantially fills said alignment holes.

10. An intermediate orthodontic attachment construction comprising a plurality of laterally interconnected attachments, each including:
    a base for attaching the attachment to a surface of a tooth;
    a body having a three-dimensional shape that includes an archwire slot and attachment member for securing an archwire thereto is formed of at least two layers of metal;
    each layer having two opposite spaced-apart major surfaces and a predetermined thickness defining a portion of at least one dimension of the body in accordance with the spacing of the surfaces and a peripheral edge face defining a second dimension of the body;
    means for fusing the layers together and to the base along said major surfaces; and
    the attachment member for securing an archwire thereto being integrally formed together with said body from at least one of the layers, the attachment member including a portion that protrudes in the second dimension outwardly from said body;
    the intermediate construction including interconnecting portions at the peripheral edge face of each layer, which portions extend in the second dimension to laterally interconnect each of the plurality of attachments, each interconnecting portion including an index hole, the index holes being aligned along a common axis for receiving an index pin.

11. An intermediate orthodontic attachment construction according to claim 10 in which the interconnecting portions of each layer include a breakoff notch adjoining the peripheral edge face of the attachment.

* * * * *